US00PP13518P2

(12) United States Plant Patent
Lemon

(10) Patent No.: US PP13,518 P2
(45) Date of Patent: Jan. 28, 2003

(54) GERANIUM PLANT NAMED 'ELEGANCE PURPLE BICOLOR'

(75) Inventor: David Lemon, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,297

(22) Filed: Jun. 8, 2001

(51) Int. Cl.[7] ..... A01H 5/00
(52) U.S. Cl. ..... Plt./331
(58) Field of Search ..... Plt./331

*Primary Examiner*—Bruce R. Campell
*Assistant Examiner*—Annette Para
(74) *Attorney, Agent, or Firm*—Webb Ziesenheim Logsdon Orkin & Hanson, P.C.

(57) ABSTRACT

A new and distinct regal geranium plant with bicolored white and purple flowers above medium green foliage.

1 Drawing Sheet

CLASSIFICATION

*Pelargonium×domesticum* (regal geranium).

VARIETAL DENOMINATION

'Elegance Purple Bicolor'.

BACKGROUND OF THE INVENTION

The present invention comprises a new and distinct cultivar of *Pelargonium×domesticum* known by the varietal name 'Elegance Purple Bicolor', Breeder No. 6DG3141-6. The new variety was discovered in Lompoc, Calif. The new variety is a result of cross breeding of 'Imperial' (U.S. Plant Pat. No. 11,596) and 'Empress' (male) (unpatented). The new variety exhibits similar flower color to Empress, but differs in its early flowering and larger flowers compared to Empress and improved habit over Imperial. The new variety was first asexually reproduced by cuttings in Connellsville, Pa. The new variety has been trial and field tested and has been found to retain its distinctive characteristics and remain true to type through successive propagations.

The new variety, when grown in a glass greenhouse in Connellsville, Pa. using full light, 60° F. night temperature and 68° F. day temperature and grown in a soilless media with constant fertilizer at 200–250 ppm nitrogen and potassium has a response time of 13 weeks to flowering from a rooted cutting to flowering in a 6 inch pot.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar at 10 weeks from a rooted cutting. The data which defines these characteristics were collected by asexual reproductions carried out at Oglevee, Ltd. in Connellsville, Pa. The color readings on a plant in a 6 inch pot were taken on Jan. 3, 2001 indoors under 200–220 foot cancles of cool white fluorescent light. Color references are primarily to The R.H.S. Colour Chart of The Royal Horticultural Society of London.

PLANT

Height: 20–22 cm from surface of media.
Growth: Upright mound, free basal branching.
Strength: Does not require artificial support.
Foliage: Stalked leaf attachment.
Leaves:
- *Size.*—6.5–7.5 cm at longest point; 8.0–9.0 cm at widest point.
- *Shape.*—Reniform; truncate base.
- *Margin.*—Serrated; slightly lobed.
- *Texture.*—Pubescent.
- *Color.*—Upper surface: Green Group 137B. Lower surface: Green Group 138B.
- *Ribs and veins.*—Type: Palmate. Color: Green Group 138B.

Petioles:
- *Color.*—Yellow-Green Group 144A.
- *Length.*—4.0–6.0 cm.

Stem/branches:
- *Color.*—Yellow-Green Group 144A.
- *Internode length.*—2.0–2.5 cm.

THE BUD

Shape and size when tightly closed, not showing color:
- *Overall.*—Elliptical cluster.
- *Individual bud.*—Elliptical.
- *Size of cluster.*—2.0–2.5 cm wide.
- *Individual bud.*—0.4–0.6 cm wide; 1.3–1.5 cm long.
- *Number of buds per cluster.*—8–10.

INFLORESCENCE

Blooming habit: Continuous flowering.
Size of fully open bloom: 9.0–11.0 cm wide.
Borne: Flowers on pedicel; pedicel on peduncle.
Number of flowers per umbel: 7–8.
Flowers:
- *Form.*—Cupped, petals overlap, slightly ruffled.
- *Size.*—6.5–7.5 cm wide; 4.0–5.0 cm deep.
- *Petals.*—Size: 2.8–4.1 cm wide; 4.0–4.5 cm long. Margin: Entire. Number per floret: 5. Shape: Obovate. Color: Upper surface: Upper two petals: Base of petal is White Group 155D with veining of Red-Purple Group 71A and Greyed-Purple Group 187A moving to a large blotch in the center the petals, most closely matched to Greyed-Purple Group 187A. Some areas of veining of Red-Purple Groups 72A and 72B below the blotch. Toward the outer edge of the petal the blotch lightens to areas of Red-Purple Group 71C, Red-Purple Groups 72B and 72A, and Purple Group 75A. It fades at the outer edge to a very light area of Purple Group 72C. Lower three petals: Outer edge is White Group 155D. In the very center is a blotch of Greyed-Purple Group 187A moving to lighter shades of purple in both directions. Toward the outer edge there are speckles and veins of shades that include Red-Purple Group 74A, Purple Group 78A, and Purple-Violet Group 81A. Toward the base of the petal the blotch is shades of Red-Purple Group 72A and Red-Purple Group 74A with veining Purple Group 78A, Greyed-Purple Group 187A, and Red-Purple Group 71A. Lower surface: Upper two petals: Base of petal is White Group 155D with veining of Purple Group 78A, Red-Purple Group 72A, and Red-Purple Group 187A. Areas of Red-Purple Groups 72A and 72B, Red-Purple Group 71A, and Red-Purple Group 74A are present on the outer edges of the blotch. Blotch of Greyed-Purple Group 187A shows through from top. Outer edge of petal is white. Lower three petals: Outer edge of petals are white with the blotch and veining showing through Red-Purple Group 74A, Greyed-Purple Group 187A, Red-Purple Groups 71A and 71C, and specks of Red-Purple Group 72A.

*Texture.*—Smooth, velvety, highly reflective.

*Tonality from a distance.*—Striking white and purple bi-colored flowers with shades of wine, deep purple, royal purple, and bright pink-orchids.

Petaloids: None observed.

Pedicel:

*Length.*—2.2–2.5 cm.

*Color.*—Yellow-Green Group 144A with Greyed-Orange Group 165A at the base of sepals.

Peduncle:

*Length.*—7.5–8.2 cm.

*Color.*—Green Group 144A.

Disease/pest resistance: No unusual susceptibility to diseases or pests has been noted to date.

Lasting quality: Flowers continuously; individual umbels last 14–21 days.

Frangrance: None.

REPRODUCTIVE ORGANS

Stamens:

*Quantity.*—7.

*Anthers.*—0.3 cm long.

*Filaments.*—Length: 1.4–1.9 cm. Color: White.

*Pollen color.*—Orange.

Pistils:

*Number.*—One.

*Length.*—2.0 cm.

*Stigma.*—Number: One. Color: Deep orchid.

*Style.*—Length: 1.4–1.5 cm. Color: Orchid.

Ovaries:

*Color.*—Pale celery green.

*Length.*—0.5 cm.

*Width.*—0.3–0.4 cm.

*Pubescence.*—Highly pubescent.

*Completeness.*—Superior.

Fruit: None observed.

I claim:

1. A new and distinct variety of regal geranium plant substantially as shown and described.

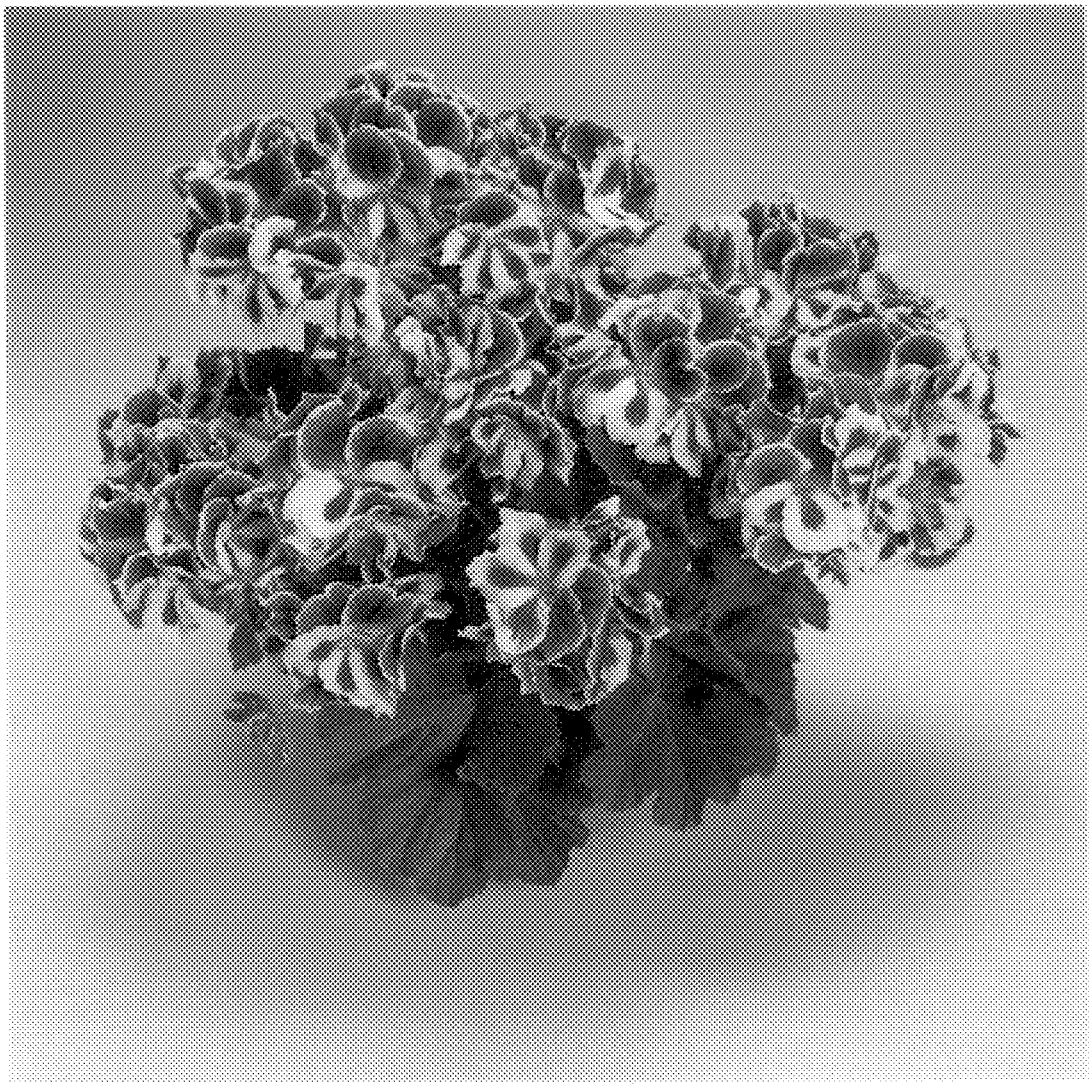

* * * * *